United States Patent
Ilyin et al.

(10) Patent No.: US 10,123,528 B2
(45) Date of Patent: Nov. 13, 2018

(54) ERYTHROCYTE PRESERVATION METHOD

(71) Applicants: Advanced Preservations Technologies, LLC, Buffalo, NY (US); Trustees of Dartmouth College, Hanover, NY (US)

(72) Inventors: Ilya Ilyin, Wayland, MA (US); Larry J. Dumont, Grantham, NH (US)

(73) Assignee: Rich Technologies Holding Company, LLC, Buffalo, NY (US)

( * ) Notice: Subject to any disclaimer, the term of this patent is extended or adjusted under 35 U.S.C. 154(b) by 705 days.

(21) Appl. No.: 14/083,581

(22) Filed: Nov. 19, 2013

(65) Prior Publication Data

US 2014/0154666 A1 Jun. 5, 2014

Related U.S. Application Data

(60) Provisional application No. 61/731,944, filed on Nov. 30, 2012.

(51) Int. Cl.
*A01N 1/02* (2006.01)
(52) U.S. Cl.
CPC .................... *A01N 1/021* (2013.01)
(58) Field of Classification Search
CPC ..................................... A01N 1/021
See application file for complete search history.

(56) References Cited

U.S. PATENT DOCUMENTS

| | | | |
|---|---|---|---|
| 4,473,552 A | 9/1984 | Jost | |
| 4,943,287 A | 7/1990 | Carmen | |
| 5,789,151 A | 8/1998 | Bitensky et al. | |
| 6,068,148 A * | 5/2000 | Weiler | A61J 1/067 141/346 |
| 2010/0009334 A1 * | 1/2010 | Ilyin | A01N 1/021 435/2 |
| 2010/0196996 A1 | 8/2010 | Kilic et al. | |
| 2012/0196362 A1 | 8/2012 | Ilyin et al. | |
| 2012/0225416 A1 | 9/2012 | Yoshida et al. | |

OTHER PUBLICATIONS

U.S. Searching Authority, International Search Report and Written Opinion, dated Mar. 20, 2014, for corresponding PCT Application No. PCT/US2013/070677.
Dumont et al., "Exploratory in vitro study of red blood cell storage containers formulated with alternative plasticizer"; Transfusion, 52:1439-1445 (Jul. 2012).

* cited by examiner

*Primary Examiner* — Teresa E Knight
(74) *Attorney, Agent, or Firm* — Fay Sharpe LLP (57) ABSTRACT

A method for preserving erythrocytes comprising the steps of obtaining an erythrocyte concentrate; subjecting the erythrocyte concentrate to a gas system that includes 65% to 100% by volume and optionally one or more ballast gases from 0% to 35% by volume; and, maintaining the erythrocyte concentrate that has been subjected to the gas system at a temperature that is above the freezing point of the erythrocyte concentrate and up to a temperature of about 30° C.

30 Claims, 2 Drawing Sheets

ERYTHROCYTE PRESERVATION METHOD

The present invention claims priority on U.S. Provisional Patent Application Ser. No. 61/731,944 filed Nov. 30, 2012, which is incorporated herein by reference.

The present invention refers to blood preservation method, particularly to the preservation of a donors' blood—namely, packed red blood cells (erythrocyte concentrate).

BACKGROUND OF THE INVENTION

The widely used erythrocyte preservation methods involve obtainment of erythrocytes from donors (e.g., using the apheresis method, or by separation from donated whole blood) in the form of packed red blood cells (erythrocyte concentrate) with reduced content of white blood cells and subsequent storage of obtained erythrocyte concentrate in plastic bags at a temperature within the range from 1° C. to 6° C. for a period of 42 days. For instance, this method is currently implemented through the use of apheresis apparatuses produced by Haemonetics Corp (Baintree, Mass., USA) and Terumo BCT, Inc. (Lakewood, Colo., USA) and assemblies of bags for blood components (also supplied together with apheresis apparatuses) manufactured of polyvinylchloride with plasticizer his (2-ethylhexyl) phthalate (DEHP, CAS No. 117-81-7). Only about 20 percent of RBC collected using this method, the majority is separated from donated whole blood). For platelets it is opposite.

The red blood cells (RBC) for transfusion are collected from donors into CPD or CP2D anticoagulant preservative solution. The RBC are separated by centrifugation method, and a solution for long term storage is added (e.g., AS-3). White blood cells are removed by filtration, and the RBC/AS-3 is stored in DEHP plasticized PVC bags at 1-6° C. for up to 42 days prior to transfusion. It is well know that the DEHP plasticizer has an important protective effect on the RBC, reducing the amount of hemolysis over the course of storage. It is desirable to minimize this storage hemolysis and other storage damage to provide the maximum therapeutic benefit to the transfusion recipient as well as minimize the potential adverse sequelae associated with RBC transfusion. The DEHP plasticizer (used for manufacturing such bags) dissolves partially in the erythrocyte concentrate in the course of storage of the RBCs, thereby diffusing from bag material and exerting additional preserving action upon the erythrocytes. It was shown (Dumont Larry J. et al. Exploratory in vitro study of red blood cell storage containers formulated with an alternative plasticizer. *Transfusion*, 2012 July 52(7):1439-1445) that the presence of DEHP plasticizer reduces the number of erythrocytes that lysed during the storage of the erythrocyte concentrate.

DEHP plasticizer in the erythrocyte concentrate decomposes into toxic components, one of which—namely, is mono-ethylhexyl phthalate (MEHP). Thus, a disadvantage of preserving erythrocytes in bags manufactured of material containing DEHP plasticizer is the danger of intoxication of patients after transfusion of a erythrocyte concentrate unit. The indicated negative consequence may increase quite significantly in the case of multiple transfusions. Taking this circumstance into account, it is preferable to store erythrocyte concentrate in bags made of materials that do not contain DEHP plasticizer. Because of theoretical adverse effects in certain high risk patient populations, it is desirable to find an alternative to DEHP as a component in RBC storage bags. However, in this case, the preserving effect (caused by the presence of DEHP plasticizer) is missing, and hence, the number of erythrocytes that lyse during storage increases.

A method for platelet preservation described in US 2010/0009334, published on Jan. 14, 2010, is known. This method involves obtaining a platelet concentrate from blood obtained from an individual, keeping the platelet plasma in a gas medium containing from 65% to 100% of xenon under pressure from 3.5 to 5 atm, subsequent cooling down of platelet concentrate to a temperature within the range from approximately 1° C. to 6° C., and storage under the conditions of the above-indicated temperature and pressure of gas medium. Platelets were obtained by apheresis. This method results in an increase in the storage period for platelets.

However, as practical experience shows, the application of this method for preserving other blood cells (e.g., erythrocytes) is characterized by a number of disadvantages. First, this method presumes the use of a gas mixture, which includes oxygen or atmospheric air in addition to xenon. However, the presence of oxygen during storage of erythrocytes stimulates erythrocytolysis (hemolysis). Hemolysis of erythrocytes during storage leads to unsatisfactory quality of final product—namely, low number of intact cells in the erythrocyte concentrate, which impairs the efficiency of the latter after transfusion to patients. Even more important are adverse effects of transfusion because of the high hemolysis in the transfused RBC. In the US, if more than 1% of the erythrocyte concentrate experiences hemolysis, the erythrocyte concentrate is considered unacceptable for blood transfusion. In other countries, the amount of hemolysis must be as low as 0.8% for the erythrocyte concentrate for the erythrocyte concentrate to acceptable for blood transfusion.

In view of the current state of the art, there is a need to develop a method for the preservation of erythrocyte concentrate that ensures storage of the latter for a period of no less than 42 days without considerable degradation of erythrocytes quality and that enables the use of plastic bags manufactured without using DEHP plasticizer.

SUMMARY OF THE INVENTION

The present invention is directed to an improved method for the preservation of erythrocyte concentrate that ensures storage of the latter for a period of no less than 42 days without considerable degradation of erythrocytes quality and that enables the use of plastic bags manufactured without using DEHP plasticizer.

The present invention is directed to a blood preservation medicine, and particularly to the preservation of packed red blood cells (erythrocyte concentrate). In one non-limiting embodiment of the invention, there is provided an erythrocyte preservation method with which the erythrocyte concentrate (obtained in advance from the whole blood and placed in a bag) is maintained in a gas system that does not include oxygen gas. In one non-limiting aspect of this embodiment, the gas system includes xenon content that naturally exists in the earth's atmosphere at sea level. In another non-limiting aspect of this embodiment, the gas system includes xenon content that is greater than about 10% by volume. In still another non-limiting aspect of this embodiment, the gas system includes xenon content that is greater than about 50% by volume. In yet another non-limiting aspect of this embodiment, the gas system includes a xenon content from about 65% to about 100% by volume. Xenon (Xe) is a noble, inert, elemental gas that is a common component of air at sea level in very small proportions (less than $1/1,000$%). It is unreactive or "inert" under normal biological conditions. Xenon is a readily diffusible gas that is neither utilized nor produced by the body. The xenon can optionally be combined with one or more ballast gases (e.g., nitrogen, noble gas, carbon dioxide) at a content from 0% to 35% by volume. The amount of oxygen that is included with the xenon gas or xenon gas and ballast gas mixture is generally less than 5% by volume, typically less than 2% by volume, more typically less than 1% by volume, still more typically less than 0.5% by volume, yet more typically less than 0.1% by volume, and still yet more typically about 0% by volume. The amount of xenon in the gas system can be any amount from 65% to 100% by volume (e.g., 65%, 65.1%, 65.2% . . . 99.8%, 99.9%, 100%) and can include any range within such values. Likewise, when one or more ballast gases are included in the gas system, the amount of ballast gas in the gas system can be any amount from 0% to 35% by volume (e.g., 0%, 0.1%, 0.2% . . . 34.8%, 34.9%, 35%) and can include any range within such values. The ballast gas, when used, is generally nitrogen and/or argon; however other inert gasses to the erythrocyte concentrate can be used. The gas system is introduced to the erythrocyte concentrate in the container to partially or fully saturate the erythrocyte concentrate with the gas system. Generally, the erythrocyte concentrate is at least about 75% saturated with the gas system, typically at least about 80% saturated with the gas system, more typically at least about 85% saturated with the gas system, still more typically at least about 90% saturated with the gas system, yet more typically at least about 95% saturated with the gas system, and still yet more typically at least about 98% saturated with the gas system. In one non-limiting arrangement, at least a portion of the container is permeable to the gas mixture so that the gas mixture can be introduced into and/or removed from the container via diffusion through the container; however, this is not required. In one non-limiting configuration, the container is in the form of a bag made of polyvinylchloride that may or may not include DEHP plasticizer. The size of the container is non-limiting. One non-limiting size is a container that can contain at least 200 ml of erythrocyte concentrate. In another non-limiting configuration, the container is positioned in a hermetically-sealed vessel equipped with a cover that is permeable to the gas mixture. The vessel may or may not be permeable to the gas mixture. The erythrocyte concentrate in the container can optionally be kept in the presence of the gas mixture and under a pressure above 1 atm without additional pumping of the gas mixture while the container is positioned in the hermetically-sealed chamber. The optional cooling of the erythrocyte concentrate in the hermetically-sealed chamber can be started from a moment of gas mixture pressure stabilization in the hermetically sealed chamber, with the stabilization resulting from saturation of erythrocyte concentrate and the gas mixture.

In one non-limiting aspect of the invention, when the gas system is introduced to the erythrocyte concentrate, the pressure of the gas system is generally no more than about 4 atm. Generally, the pressure of the gas system is at least about 1 atm. For purposes of this invention, atmospheric pressure is 1 atm (760 torr). Generally, the pressure of the gas system is less than about 10 atm. In one non-limiting embodiment of the invention, the pressure of the gas system when being introduced to the erythrocyte concentrate is about 1 to 4 atm (e.g., 1 atm, 1.1. atm, 1.2 atm . . . 3.8 atm, 3.9 atm, 4 atm) and can include any range within such values. In one non-limiting aspect of the invention, the pressure of the gas system when being introduced to the erythrocyte concentrate is greater than atmospheric pressure (e.g., 1 atm).

In another and/or alternative non-limiting aspect of the invention, the gas system can be introduced to the erythrocyte concentrate when the erythrocyte concentrate is at a temperature that is above the freezing point of the erythrocyte concentrate up to a temperature of about 30° C. (e.g., 0.01° C., 0.02° C. . . . 29.98° C., 29.99° C., 30° C.). The temperature of the erythrocyte concentrate in a container can be maintained at a constant temperature or be varied (e.g., decreased, increased, etc.) while the gas system is being introduced to the erythrocyte concentrate. In one non-limiting embodiment, the gas system is introduced to the erythrocyte concentrate when the erythrocyte concentrate is at a temperature that is up to a temperature of about 25° C. In another non-limiting embodiment, the gas system is introduced to the erythrocyte concentrate when the erythrocyte concentrate is at a temperature that is up to a temperature of about 23° C. In another non-limiting embodiment, the gas system is introduced to the erythrocyte concentrate when the erythrocyte concentrate is at a temperature that is about 6° C. to 23° C.

In still another and/or alternative non-limiting aspect of the invention, the gas system is generally introduced to the erythrocyte concentrate within about 98 hours (e.g., 0.01 hours, 0.02 hours . . . 97.98 hours, 97.99 hours, 98 hours) after the blood has been removed from a human or other type of mammal. In one non-limiting embodiment, gas system is introduced to the erythrocyte concentrate within about 72 hours after the blood has been removed from a human or other type of mammal. In another non-limiting embodiment, gas system is introduced to the erythrocyte concentrate within about 48 hours after the blood has been removed from a human or other type of mammal. In another non-limiting embodiment, gas system is introduced to the erythrocyte concentrate within about 24 hours after the blood has been removed from a human or other type of mammal.

In yet another non-limiting aspect of the invention, oxygen is removed or purged from the container that includes the erythrocyte concentrate prior to the gas system (i.e., xenon, xenon plus ballast gas) being introduced to the erythrocyte concentrate; however, this is not required. Generally, the erythrocyte concentrate is exposed to a vacuum environment (e.g., 0 atm, 0.01 atm, 0.02 atm . . . 0.97 atm, 0.98 atm, 0.99 atm) for a sufficient period of time (e.g., 0.1 seconds, 0.2 seconds, 0.3 seconds . . . 599.8 seconds, 599.9 seconds, 600 seconds) to remove at least about 75% of the oxygen from the container that includes the erythrocyte concentrate, typically at least about 80% of the oxygen from the container that includes the erythrocyte concentrate, more typically at least about 85% of the oxygen from the container that includes the erythrocyte concentrate, still more typically at least about 90% of the oxygen from the container that includes the erythrocyte concentrate, and yet more typically at least about 95% of the oxygen from the container that includes the erythrocyte concentrate. As such, anywhere from 75% to 100% (e.g., 75%, 75.1%, 75.2% . . . 99.8%, 99.9%, 100%) of the oxygen is removed from the container that includes the erythrocyte concentrate prior to the gas system being introduced to the erythrocyte concentrate. The degree of the vacuum and the time period that the erythrocyte concentrate is subjected to the vacuum is non-limiting. The method of removing or purging the oxygen from the container that includes erythrocyte concentrate also results in the removal of oxygen that is dissolved in the erythrocyte concentrate.

In still yet another and/or alternative non-limiting aspect of the invention, once the gas system is introduced to the erythrocyte concentrate, the erythrocyte concentrate is maintained at a refrigerated temperature (i.e., less than ambient temperature) that is above the freezing point of the erythrocyte concentrate. Generally, the refrigerated temperature is no more than about 25° C., typically no more than about 20° C., more typically no more than about 15° C., still more typically no more than about 10° C., and yet more typically no more than about 6° C. In one non-limiting embodiment, the erythrocyte concentrate can be maintained at such refrigerated temperature for at least about 42 days and results in hemolysis of the erythrocyte concentrate of no more than about 1%, generally results in hemolysis of the erythrocyte concentrate of no more than about 0.8%, typically results in hemolysis of the erythrocyte concentrate of no more than about 0.7%, and more typically results in hemolysis of the erythrocyte concentrate of no more than about 0.6%.

In another and/or alternative non-limiting aspect of the invention, the gas system can optionally be introduced to the erythrocyte concentrate more than one time prior to refrigerating the erythrocyte concentrate. When the gas system is introduced to the erythrocyte concentrate more than one time prior to refrigerating the erythrocyte concentrate, the erythrocyte concentrate is pressurized with the gas system, then purged of the gas system, and then again pressurized with the gas system. The number of pressurizing and purging steps is non-limiting. Generally, the erythrocyte concentrate is not pressurized, purged and then repressurized more than 5 times, and typically no more than 4 times, more typically no more than 3 times, and still yet more typically no more than 2 times. The purging of the gas system from the erythrocyte concentrate can be conducted under a vacuum; however, this is not required. The pressurizing of the erythrocyte concentrate with the gas system, then purging of the gas system, and then again pressurizing with the gas system is used to further remove any oxygen remaining in the erythrocyte concentrate after the erythrocyte concentrate was initially purged of air prior to first introducing the gas system to the erythrocyte concentrate. The purging of the gas system from the erythrocyte can occur under similar parameters as the removal of the oxygen form the erythrocyte concentrate; however, this is not required. The erythrocyte concentrate can be optionally agitated or otherwise shaken to facilitate in the removal of the oxygen from the erythrocyte concentrate.

In still another and/or alternative non-limiting aspect of the invention, the erythrocyte concentrate, after being pressurized with the gas system, and prior to and/or during the refrigeration of the erythrocyte concentrate, can optionally be agitated or otherwise shaken to facilitate in the mixing of the gas system with the erythrocyte concentrate. The time of agitation can be from about 0.002 hours to 24 hours (e.g., 0.0021 hours, 0.0022 hours . . . 23.99 hours, 24 hours). In one non-limiting embodiment, the time of agitation is no more than about 10 hours, typically no more than about 5 hours, and more typically no more than about 3.5 hours.

In yet another and/or alternative non-limiting aspect of the invention, after the refrigeration period of the erythrocyte concentrate is completed, and prior to or after the erythrocyte concentrate has been depressurized of the gas system, the erythrocyte concentrate can optionally be agitated. In one non-limiting embodiment, the erythrocyte concentrate is agitated prior to depressurizing the erythrocyte concentrate of the gas system. The time of agitation can be from about 0.002 hours to 10 hours (e.g., 0.0021 hours, 0.0022 hours . . . 9.99 hours, 9 hours). In one non-limiting embodiment, the time of agitation is no more than about 2 hours, typically no more than about 1 hour, more typically no more than about 0.5 hours, and still more typically no more than about 0.2 hours.

In still yet another and/or alternative non-limiting aspect of the invention, after the erythrocyte concentrate has been depressurized of the gas system and optionally agitated, the erythrocyte concentrate is optionally allowed to warm from the refrigerated temperature to ambient temperature (e.g., 25° C.-27° C.). In one non-limiting embodiment, the time period that the erythrocyte concentrate is allowed to warm can be from about 0.002 hours to 10 hours (e.g., 0.0021 hours, 0.0022 hours . . . 9.99 hours, 9 hours). As can be appreciated, longer warming times can be used.

In another and/or alternative non-limiting aspect of the invention, after the erythrocyte concentrate has been depressurized of the gas system, and optionally agitated, the erythrocyte concentrate is used in a blood transfusion within about 72 hours, typically within about 36 hours, more typically within about 24 hours, and still more typically within about 12 hours.

In still another non-limiting aspect of the invention, the container used for the erythrocyte concentrate does not include DEHP plasticizer. The method of the present invention is able to preserve erythrocyte concentrate for at least about 42 days with hemolysis of the erythrocyte concentrate of no more than about 1% in a container that does not include DEHP plasticizer. Such method is a significant advancement over prior preservation methods that require the preservative effects of DEHP plasticizer to obtain preservation times of 42 days for the erythrocyte concentrate. The method of the present invention overcomes this former limitation in the art of preserving erythrocyte concentrate.

One non-limiting object of the present invention is the provision of a method for preserving an erythrocyte concentrate.

Another and/or alternative non-limiting object of the present invention is the provision of a method for preserving an erythrocyte concentrate without the use of a container manufactured that includes DEHP plasticizer.

Still another and/or alternative non-limiting object of the present invention is the provision of a method for preserving an erythrocyte concentrate by use of a gas system that includes xenon gas.

Yet another and/or alternative non-limiting object of the present invention is the provision of a method for preserving an erythrocyte concentrate by use of a gas system that includes xenon gas and the erythrocyte concentrate has been partially or fully purged of oxygen.

Still yet another and/or alternative non-limiting object of the present invention is the provision of a method for the preservation of the erythrocyte concentrate that ensures storage of the latter for a period of no less than 42 days without considerable degradation of erythrocytes quality and that enables the use of plastic bags manufactured without using DEHP plasticizer.

Another and/or alternative non-limiting object of the present invention is the provision of a method for the preservation of the erythrocyte concentrate that reduces hemolysis of the erythrocyte concentrate.

Still another and/or alternative non-limiting object of the present invention is the provision of a method for the preservation of the erythrocyte concentrate that improves that adenosine triphosphate (ATP) content of the erythrocyte concentrate.

Yet another and/or alternative non-limiting object of the present invention is the provision of an erythrocyte container system designed to preserve erythrocytes that includes a container having an erythrocyte concentrate, and the erythrocyte concentrate in the container is at a temperature of less than ambient temperature, and the erythrocyte concentrate is at least partially saturated with a gas system that includes xenon gas.

These and other objects, features and advantages of the present invention will become apparent in light of the following detailed description of preferred embodiments thereof, as illustrated in the accompanying drawings.

DETAILED DESCRIPTION OF THE INVENTION

Referring now to the drawings wherein the showings are for the purpose of illustrating embodiments of the invention only and not for the purpose of limiting the same, the present invention is directed to an improved method for the preservation of erythrocyte concentrate. The improved method for the preservation of erythrocyte concentrate can be accomplish with or with the use of container manufactured without using DEHP plasticizer. The method includes the use of a gas system that is introduced to the erythrocyte concentrate during storage of the erythrocyte concentrate. The present invention is also directed to an erythrocyte container system designed to preserving erythrocytes comprising a container that includes an erythrocyte concentrate, and the erythrocyte concentrate is at least partially saturated with a gas system, and the gas system including xenon gas at a concentration that is greater than xenon gas that naturally occurs in the atmosphere.

Several non-limiting methods in accordance with the present inventions are set forth as follows:

Method A

1. Obtain an erythrocyte concentrate in a container;
2. Subject the erythrocyte concentrate in a container to a gas system that includes xenon gas at a concentration that is greater than xenon gas that naturally occurs in the atmosphere; and,
3. Maintain the erythrocyte concentrate that has been subjected to the gas system at a temperature that is above the freezing point of the erythrocyte concentrate up to a temperature of about 30° C.

As can be appreciated, the RBC can be exposed to xenon gas during and/or after the RBC are inserted into the container.

Method B

1. Obtain an erythrocyte concentrate in a container;
2. Subject the erythrocyte concentrate in a container to a gas system that includes xenon gas at a concentration of 65% to 100% by volume and optionally includes one or more ballast gases from 0% to 35% by volume; and,
3. Maintain the erythrocyte concentrate that has been subjected to the gas system at a temperature that is above the freezing point of the erythrocyte concentrate up to a temperature of about 30° C.

Method C

1. Obtain an erythrocyte concentrate in a container;
2. Remove 70-100% of the oxygen from the erythrocyte concentrate in the container that includes the erythrocyte concentrate;
3. Subject the erythrocyte concentrate in the container to a gas system that includes xenon gas at a concentration that is greater than xenon gas that naturally occurs in the atmosphere after the oxygen removal step; and,
4. Maintain the erythrocyte concentrate that has been subjected to the gas system at a temperature that is above the freezing point of the erythrocyte concentrate up to a temperature of about 30° C.

Method D

1. Obtain an erythrocyte concentrate in a container;
2. Remove 70-100% of the oxygen from the erythrocyte concentrate in the container that includes the erythrocyte concentrate;
3. Subject the erythrocyte concentrate in the container to a gas system that includes xenon gas at a concentration of 65% to 100% by volume and optionally includes one or more ballast gases from 0% to 35% by volume; and,
4. Maintain the erythrocyte concentrate that has been subjected to the gas system at a temperature that is above the freezing point of the erythrocyte concentrate up to a temperature of about 30° C.

In Methods A-D, the pressure of the gas system when being introduced to the erythrocyte concentrate in a container is generally less than 6 atm, typically 1-4 atm, more typically 1-3 atm, and still more typically 1-2 atm. In Methods A-D, the temperature of the erythrocyte concentrate in the container when the gas system is being introduced to the erythrocyte concentrate is generally no greater than about 25° C., and typically no greater than about 23° C. In Methods A-D, the temperature of the erythrocyte concentrate in the container can be maintained at a constant temperature or be varied (e.g., decreased, etc.) while the gas system is being introduced to the erythrocyte concentrate in a container. In Methods A-D, the container that includes the erythrocyte concentrate can optionally be agitated or shaken prior to, during and/or after the gas system is introduced to the erythrocyte concentrate in the container. In Methods A-D, the container that includes the erythrocyte concentrate can be cooled to a temperature of no more than about 6° C. and greater than the freezing point of the erythrocyte concentrate after the gas system is introduced to the erythrocyte concentrate in the container. In Methods A-D, the container can optionally be absent DEHP plasticizer.

More specific non-limiting methods of the invention are as follows:

Method E

1. Obtain an erythrocyte concentrate in a container;
2. Remove 70-100% of the oxygen from the erythrocyte concentrate in the container in a vacuum environment;
3. Subject the erythrocyte concentrate in the container to a gas system that includes 65% to 100% by volume xenon and optionally one or more ballast gases from 0% to 35% by volume after the oxygen removal step at a temperature of no more than about 23° C. and at a pressure of greater than 1 atm and up to about 4 atm; and 4. Maintain the erythrocyte concentrate that has been subjected to the gas system at a temperature that is above the freezing point of the erythrocyte concentrate and up to about 6° C.

Method F

1. Obtain an erythrocyte concentrate in a container;
2. Remove 70-100% of the oxygen from the erythrocyte concentrate in the container in a vacuum environment;
3. Subject the erythrocyte concentrate in a container to a gas system that includes 65% to 100% by volume xenon and optionally one or more ballast gases from 0% to 35% by volume after the oxygen removal step at a temperature of about 18° C. to 23° C. and at a pressure of about 1.01-2 atm;
4. Cool the erythrocyte concentrate in a container to a temperature that is above the freezing point of the erythrocyte concentrate and up to about 6° C., and,
5. Maintain the erythrocyte concentrate that has been subjected to the gas system at a temperature that is above the freezing point of the erythrocyte concentrate up to a temperature of about 6° C. for up to 42 days.

Method G

1. Obtain an erythrocyte concentrate in a container wherein the container is absent DEHP plasticizer;
2. Remove 70-100% of the oxygen from the erythrocyte concentrate in the container in a vacuum environment;
3. Subject the erythrocyte concentrate in a container to a gas system that includes 65% to 100% by volume xenon and optionally one or more ballast gases from 0% to 35% by volume after the oxygen removal step at a temperature of about 18° C. to 23° C. and at a pressure of about 1.01-2 atm;
4. Agitate or shake the erythrocyte concentrate in a container prior to, during and/or after the gas system is introduced to the erythrocyte concentrate in a container;
5. Cool the erythrocyte concentrate in a container to a temperature that is above the freezing point of the erythrocyte concentrate and up to about 6° C., and,
6. Maintain the erythrocyte concentrate that has been subjected to the gas system at a temperature that is above the freezing point of the erythrocyte concentrate up to a temperature of about 6° C. for up to 42 days.

In Methods E-G, the pressure of the gas system when being introduced to the erythrocyte concentrate in a container is generally less than 6 atm, typically 1-4 atm, more typically 1-3 atm, and still more typically 1-2 atm. In Methods E-G, the temperature of the erythrocyte concentrate in the container when the gas system is being introduced to the erythrocyte concentrate is generally no greater than about 25° C., and typically no greater than about 23° C. In Methods E-G, the temperature of the erythrocyte concentrate in the container can be maintained at a constant temperature or be varied (e.g., decreased, etc.) while the gas system is being introduced to the erythrocyte concentrate in a container. In Methods E-G, the container that includes the erythrocyte concentrate can optionally be agitated or shaken prior to, during and/or after the gas system is introduced to the erythrocyte concentrate in the container. In Methods E-G, the container that includes the erythrocyte concentrate can be cooled to a temperature of no more than about 6° C. and greater than the freezing point of the erythrocyte concentrate after the gas system is introduced to the erythrocyte concentrate in the container. In Methods E-G, the container can optionally be absent DEHP plasticizer.

While not being held to any one theory of the method of the present invention, it is believed that diffusion of gases into erythrocyte concentrate (including erythrocytes proper) takes place when erythrocyte concentrate is kept in a gas mixture of above-indicated composition under pressure (e.g., 2 atm). Saturation of erythrocyte concentrate with xenon under the conditions of above-indicated pressure ensures subsequent storage of the former at a temperature that is above the freezing point and up to about 6° C. with preservation of viability and functionality of erythrocytes. The preserving action of xenon on erythrocytes ensures storage of erythrocyte concentrate for a period of up to 42 days, which allows for giving up the idea of using plastic bags manufactured with the use of DEHP plasticizer.

Also, in contrast to the known methods, the proposed method eliminates diffusion of oxygen from the ambient environment through bag material into the erythrocyte concentrate, which reduces hemolysis of erythrocytes.

A cooling chamber can optionally be used for cooling the erythrocyte concentrate down and for subsequent storage of cooled erythrocyte concentrate.

When implementing the proposed method, the erythrocyte concentrate can be placed into a container permeable for the gas mixture, and keeping of erythrocyte concentrate in the gas mixture is carried out in a hermetically-sealed chamber, into which the container with erythrocyte concentrate is placed. In particular, prior to feeding gas mixture into the hermetically-sealed chamber (in which a container with erythrocyte concentrate was placed), the chamber is vacuumed with the aim to remove oxygen from it.

A hermetically-sealed vessel equipped with a cover permeable for gas mixture or bag made of material permeable for gas mixture (e.g. bags that are manufactured of polyvinylchloride without DEHP and that are usually used for the storage of blood components) can optionally be used as a container for erythrocyte concentrate.

The time period during which erythrocyte concentrate is kept in a gas mixture under the pressure (e.g., 1.01-4 atm) is determined by the desired level of erythrocyte concentrate saturation with xenon (as indicated above). For instance, when using a bag made of material permeable for the gas mixture, into which at least 200 ml of erythrocyte concentrate is placed, then subjected to a pressure above 1 atm, this time will be at least about 1 minute, typically less than about 30 hours, more typically at least about 15 minutes, more typically at least about 30 minutes, still more typically at least about 1 hour, and yet still more typically at least about 3 hours.

In the general case, duration of keeping the erythrocyte concentrate in a gas mixture under the pressure (e.g., 1.01 atm, 1.5 atm, 2 atm, etc.) can be determined based on cessation of gas mixture pressure decrease in the hermetically-sealed chamber (without additional pumping of gas mixture), which indicates on cessation of erythrocyte concentrate saturation with gas mixture components. Cooling the erythrocyte concentrate down can optionally be started from the moment of gas mixture pressure stabilization in the hermetically-sealed chamber.

Immediately prior to using the erythrocyte concentrate after storage, the erythrocyte concentrate can optionally be kept under pressure not exceeding atmospheric pressure (1 atmosphere) and at a temperature from 18° C. to 28° C. (e.g., warm to ambient temperature, etc.) for at least a period that is sufficient for natural heating of erythrocyte concentrate to the above-indicated temperature; however, this is not required. In particular, the hermetically-sealed chamber can be taken out from the cooling chamber, hermetic sealing is unsealed, and then the bag with erythrocyte concentrate is extracted and kept at room temperature and atmospheric pressure for a time period sufficient for natural heating of erythrocyte concentrate to room temperature and for outgoing of the gas system from erythrocyte concentrate as the erythrocyte concentrate warms to ambient temperature in an environment. To reduce the time period during which gas mixture components are released or escape from the erythrocyte concentrate after the storage period of the container, the container that includes the erythrocyte concentrate can optionally be agitated or shaken and/or be placed under the conditions of decreased pressure or a vacuum (as compared to the atmospheric pressure).

The present invention could be used in practice for the purpose of preserving erythrocytes (in the form of erythrocyte concentrate) with the use of conventional bags intended for storing blood products and made of a material that is gas-permeable for xenon and which bag does not contain DEHP plasticizer. Standard equipment capable of supplying the gas system into a hermetically-sealed chamber that can withstand the pressure of the gas system of up to 2-4 atm can be used in the present invention. Standard refrigerating equipment (conventional refrigerators) in which preserved blood products are stored can also be used in the present invention.

The possibility of practical implementation of the present invention and obtainment of the above-indicated results (in terms of preserving 200 ml of erythrocyte concentrate during a period of up to 42 days while keeping the low level of erythrocytes hemolysis) has been verified experimentally.

Figure 1:
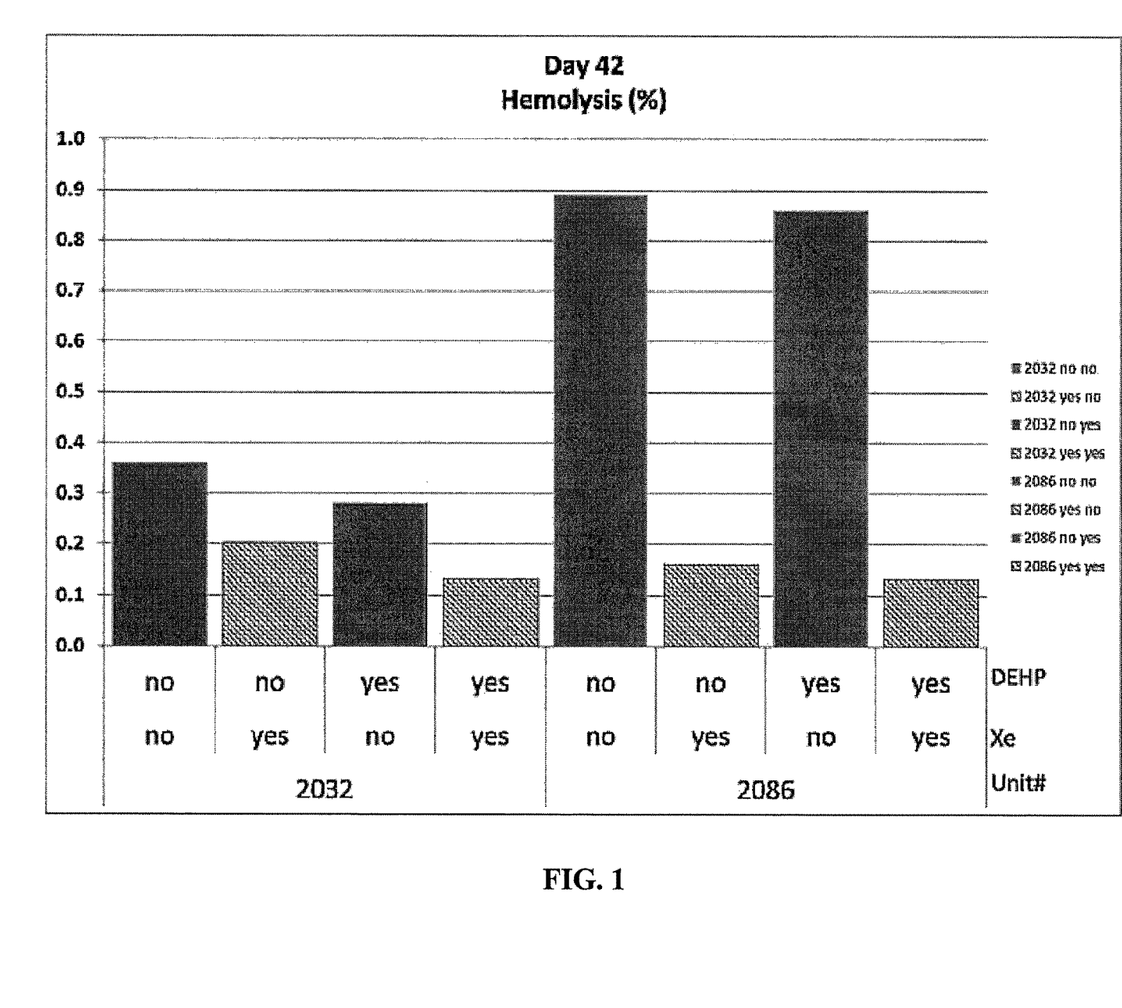
FIG. 1 is a graph that illustrates the degree of hemolysis of a bag of erythrocyte concentrate after 42 days when exposed and not exposed to the gas system of the present invention; and, FIG. 2 is a graph that illustrates the ATP content of a bag of erythrocyte concentrate after 42 days when exposed and not exposed to the gas system of the present invention.
Figure 2:
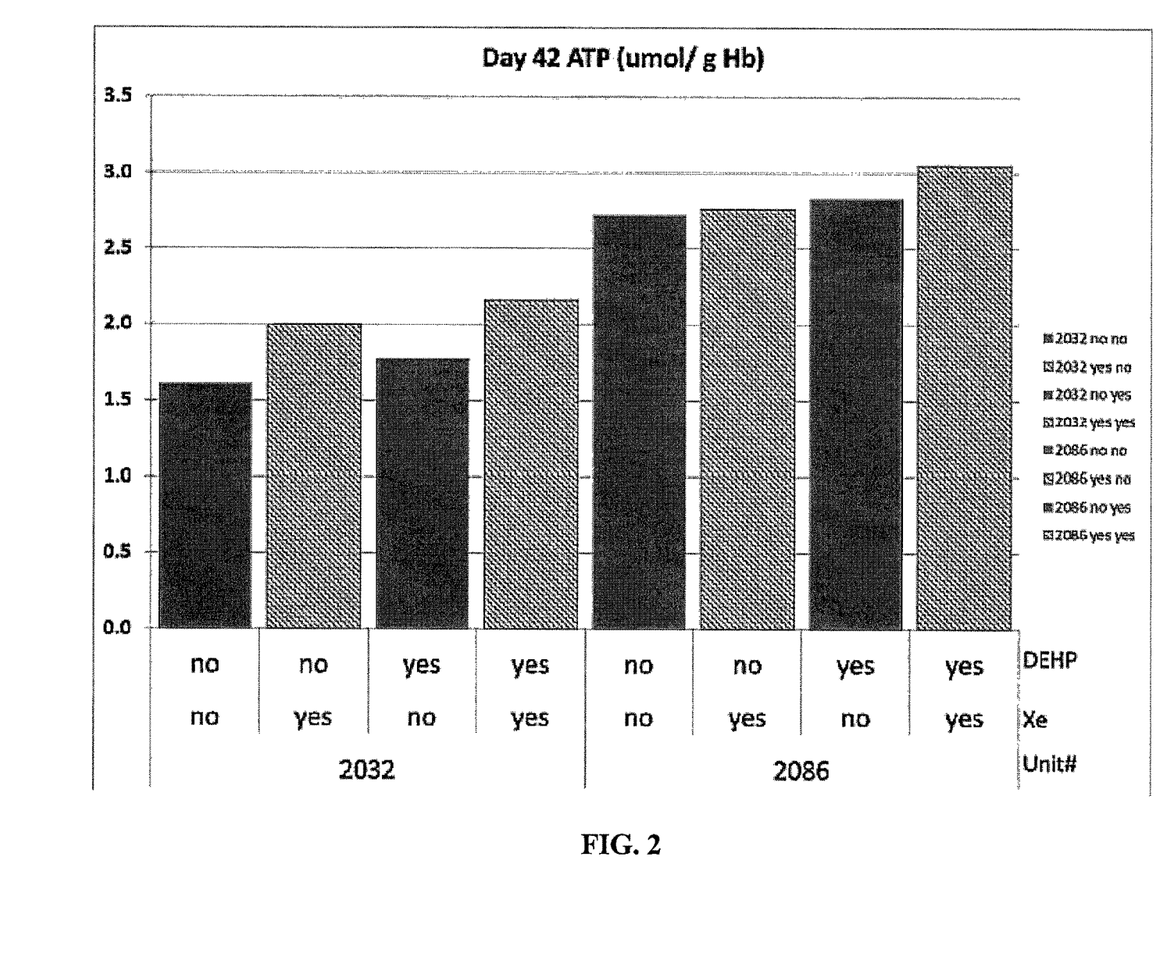

Referring now to FIGS. 1-2, test results of two different erythrocyte concentrates are illustrated. The first erythrocyte concentrate is identified by, number 2032 and the second erythrocyte concentrate is identified by number 2086. Each of the samples was divided into four different containers. Two of the containers for each of the samples included DEHP plasticiser and two of the containers for each of the samples did not include DEHP plasticiser. Also, for each sample, two of the containers included a gas system of 99.9% by volume xenon gas. The graphs indicate which container included or were absent xenon gas and/or DEHP plasticiser. The testing protocol for the containers was as follows:

For Containers That Are Absent Xe Gas:
a. Place non-Xe units flat on a rotator for 3.5 hours.
b. Place non-Xe units in blood bank refrigerator at the same time as the Xe units.

For Containers That Include Xe Gas:
a. Place Xe units flat in a pretested hyperatmic chamber.
b. Evacuate the chamber with vacuum to remove oxygen from the Xe units.
c. Pressurize the chamber with Xe gas at 4 atm.
d. Vent the chamber of Xe gas.
e. Pressurize the chamber with Xe gas at 4 atm.
f Vent the chamber of Xe gas.
g. Pressurize the chamber with Xe gas at 4 atm.
h. Vent the chamber of Xe gas.
i. Pressurize the chamber with Xe gas at 4 atm.
j. Place the pressurized Xe unit on an agitator for 3.5 h.
k. Place the pressurized Xe unit in a blood bank refrigerator at the same time as the non-Xe units.

While the Xe units and non-Xe units are in the blood bank refrigerator, the Xe units were periodically checked over a 42 day period to ensure that the pressure in the Xe units exceeded 1 atm. After 42 days, all of the units were removed from the blood bank refrigerator. After the units were removed from the blood bank refrigerator, the following procedures where conducted on the units:

1. Immediately place the pressurized Xe units and non-Xe units on a platelet to and-fro horizontal agitator for 10 minutes.
2. Depressurize all of the units by opening a value on the container.
3. Place all units on a bench top and hold for 3 hours.
4. Following the 3 hour hold period, test the samples for percentage of hemolysis and the ATP content.

As is illustrated in FIG. 1, the percent of hemolysis of the erythrocyte concentrate samples that were treated with xenon gas is less than the samples that were not treated with the xenon gas. In both samples, the percent of hemolysis of the erythrocyte concentrate samples that were treated with xenon gas is significantly less that the non-treated samples. Reduced amounts of hemolysis is also present with container that include DEHP plasticiser. Also, lower amounts of hemolysis were achieved by use the xenon gas with no DEHP plasticiser as compared to a container that included DEHP plasticiser and no xenon gas. The addition of DEHP plasticiser to a container that included xenon gas resulted in a further reduction of hemolysis.

Referring now to FIG. 2, both samples indicated a higher ATP content in the erythrocyte concentrate when treated with xenon gas.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween. The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

What is claimed:

1. A method for preserving erythrocytes for later transfusion by reducing hemolysis and increasing the ATP content of stored erythrocyte concentrate comprising the steps of:
   a. obtaining an erythrocyte concentrate for use in a transfusion;
   b. placing said erythrocyte concentrate in a container, said container permeable to gas, said container containing said erythrocyte concentrate, and said container absent a plasticizer that includes bis (2-ethylhexyl) phthalate;
   c. removing at least 70% of oxygen from the erythrocyte concentrate while said erythrocyte concentrate is in said container, said oxygen removed from said erythrocyte concentrate and said container by diffusion of said oxygen through said container;

d. subjecting the erythrocyte concentrate while in said container to a gas system at a pressure of at least 1 atm, and less than 6 atm, to thereby cause said gas system to diffuse through said container and interact with said erythrocyte concentrate in said container, said gas system includes xenon, said step of subjecting said erythrocyte concentrate to said gas system occurring after said step of removing oxygen from said erythrocyte concentrate, said xenon in said gas system at a concentration of 65% to 100% by volume, said gas system added to said erythrocyte concentrate at a temperature of not more than about 30° C.;

e. cooling and then maintaining the erythrocyte concentrate that has been subjected to the gas system at a temperature that is above the freezing point of the erythrocyte concentrate and up to a temperature of about 6° C.; and, f. maintaining said erythrocyte concentrate in said container for a period of up to 42 days without considerable degradation of erythrocytes quality and with less than 0.8% hemolysis of said erythrocytes such that said erythrocyte concentrate in said container can be used for said later transfusion.

2. The method as defined in claim 1, wherein said gas system includes less than 5% by volume oxygen.

3. The method as defined in claim 1, wherein 70-100% of the oxygen from the erythrocyte concentrate is removed prior to adding said gas system to said erythrocyte concentrate.

4. The method as defined in claim 3, wherein said step of removing oxygen occurs in a vacuum environment.

5. The method as defined in claim 1, wherein said gas system is added to said erythrocyte concentrate at a pressure of at least 1 to about 2 atm.

6. The method as defined in claim 1, wherein said gas system is added to said erythrocyte concentrate at a pressure of at least 1 to about 3 atm.

7. The method as defined in claim 1, wherein said erythrocyte concentrate is absent bis (2-ethylhexyl) phthalate plasticizer.

8. The method as defined in claim 1, further including the step of agitating said erythrocyte concentrate in a container a) prior to addition of said gas system to said erythrocyte concentrate, b) after said addition of said gas system to the erythrocyte concentrate, and combinations thereof.

9. The method as defined in claim 1, wherein the pressure of the gas system when being introduced to said erythrocyte concentrate is 1-4 atm.

10. The method as defined in claim 1, wherein a temperature of said erythrocyte concentrate when said gas system is introduced to said erythrocyte concentrate is above the freezing point of the erythrocyte concentrate and no greater than about 23° C.

11. The method as defined in claim 10, wherein said temperature of said erythrocyte concentrate is maintained at a constant temperature or has a variable temperature while said gas system is introduced to said erythrocyte concentrate.

12. The method as defined in claim 1, wherein a temperature of said erythrocyte concentrate after addition of said gas system is no greater than about 20° C.

13. The method as defined in claim 12, wherein said step of cooling said erythrocyte concentrate after addition of said gas system occurs in a cooling chamber, said cooling chamber is designed to store said cooled erythrocyte concentrate for up to 42 days.

14. The method as defined in claim 1, wherein said gas system includes 0.1-35% of at least one ballast gas and said ballast gas is nitrogen, argon or mixtures thereof.

15. The method as defined in claim 1, wherein at least a portion of said container is permeable to said gas mixture and said gas mixture is introduced into and removed from said container via diffusion through said container.

16. The method as defined in claim 1, wherein said container is positioned in a hermetically-sealed vessel equipped with a cover that is permeable to said gas mixture, and said vessel is not permeable to said gas mixture.

17. The method as defined in claim 1, wherein said erythrocyte concentrate in said container is kept in said gas mixture and under a pressure above 1 atm without additional pumping of said gas mixture while said container is positioned in said hermetically-sealed chamber, and cooling of erythrocyte concentrate is started from a moment of gas mixture pressure stabilization in said hermetically-sealed chamber, with said stabilization resulting from saturation of erythrocyte concentrate said gas mixture.

18. The method as defined in claim 1, wherein a bag is made of polyvinylchloride.

19. A method for preserving erythrocytes for later transfusion by reducing hemolysis and increasing the ATP content of stored erythrocyte concentrate comprising the steps of:

a. obtaining an erythrocyte concentrate that is positioned in a gas permeable bag, said erythrocyte concentrate and said bag absent a plasticizer that includes bis (2-ethylhexyl) phthalate;

b. removing 70-100% of the oxygen from the erythrocyte concentrate, said step of removing oxygen from the erythrocyte concentrate occurs while said erythrocyte concentrate is in said bag, said oxygen removed from said erythrocyte concentrate and said bag by diffusion of said oxygen through said bag;

c. subjecting the erythrocyte concentrate to a gas system while in said bag at a pressure of at least 1 atm, and less than 6 atm, to thereby cause said gas system to diffuse through said bag and interact with said erythrocyte concentrate in said bag, said gas system added to said erythrocyte concentrate at a pressure of above 1 atm, a temperature of said erythrocyte concentrate when said gas system is introduced to said erythrocyte concentrate is above the freezing point of said erythrocyte concentrate and no greater than about 23° C., said gas system includes 65-100% by volume xenon, 0-35% by volume of at least one ballast gas, and less than 5% by volume oxygen, said ballast gas including one or more gasses selected from the group consisting of nitrogen, noble gas other than xenon, and carbon dioxide, said step of removing oxygen from the erythrocyte concentrate occurring prior to said step of adding said gas system to said erythrocyte concentrate;

d. cooling said erythrocyte concentrate after addition of said gas system to a temperature above the freezing point of the erythrocyte concentrate and no greater than about 6° C.; and, e. maintaining said erythrocyte concentrate in said container for a period of up to 42 days without considerable degradation of erythrocytes quality and with less than 0.8% hemolysis of said erythrocytes such that said erythrocyte concentrate in said container can be used for said later transfusion.

20. The method as defined in claim 19, wherein said step of removing oxygen occurs in a vacuum environment.

21. The method as defined in claim 20, wherein said gas system is added to said erythrocyte concentrate at a pressure of at least 1 to about 4 atm.

22. The method as defined in claim 21, further including the step of agitating said erythrocyte concentrate in a container a) prior to addition of said gas system to said erythrocyte concentrate, b) after said addition of said gas system to the erythrocyte concentrate, and combinations thereof.

23. The method as defined in claim 19, wherein said gas system is added to said erythrocyte concentrate at a pressure of at least 1 to about 4 atm.

24. The method as defined in claim 19, further including the step of agitating said erythrocyte concentrate in a container a) prior to addition of said gas system to said erythrocyte concentrate, b) after said addition of said gas system to the erythrocyte concentrate, and combinations thereof.

25. The method as defined in claim 19, wherein said step of cooling said erythrocyte concentrate occurs in a cooling chamber and said cooled erythrocyte concentrate is stored in said cooling chamber for up to 42 days.

26. The method as defined in claim 25, wherein said container is positioned in a hermetically-sealed vessel equipped with a cover that is permeable to said gas mixture, said vessel is not permeable to said gas mixture.

27. The method as defined in claim 26, wherein said erythrocyte concentrate in said container is kept in said gas mixture and under a pressure above 1 atm without additional pumping of said gas mixture while said container is positioned in said hermetically-sealed chamber, and cooling of erythrocyte concentrate is started from a moment of gas mixture pressure stabilization in said hermetically-sealed chamber, said stabilization resulting from saturation of erythrocyte concentrate with said gas mixture.

28. The method as defined in claim 19, wherein said container is positioned in a hermetically-sealed vessel equipped with a cover that is permeable to said gas mixture, said vessel is not permeable to said gas mixture.

29. The method as defined in claim 19, wherein said erythrocyte concentrate in said container is kept in said gas mixture and under a pressure above 1 atm without additional pumping of said gas mixture while said container is positioned in said hermetically-sealed chamber, and cooling of erythrocyte concentrate is started from a moment of gas mixture pressure stabilization in said hermetically-sealed chamber, said stabilization resulting from saturation of erythrocyte concentrate with said gas mixture.

30. A method for preserving erythrocytes for later transfusion by reducing hemolysis and increasing the ATP content of stored erythrocyte concentrate comprising the steps of:
  a. obtaining a container of erythrocyte concentrate for use in a transfusion, said container permeable to gas, said erythrocyte concentrate and said container absent a plasticizer that includes bis (2-ethylhexyl) phthalate;
  b. removing at least 70% of oxygen from the erythrocyte concentrate while said erythrocyte concentrate is in said container, said oxygen removed from said erythrocyte concentrate and said container by diffusion of said oxygen through said container by subjecting said container to a vacuum environment, said step of subjecting said erythrocyte concentrate to said gas system occurring after said step of removing oxygen from said erythrocyte concentrate;
  c. subjecting said erythrocyte concentrate while in said container to a gas system at a pressure of 1.01-2 atm. at a temperature of 18-23° C. to thereby cause said gas system to diffuse through said container and interact with said erythrocyte concentrate in said container, said gas system includes 65-100 vol. % xenon, 0-35 vol. % ballast gas and less than 5 vol. % oxygen, said ballast gas including one or more gasses selected from the group consisting of nitrogen, noble gas other than xenon, and carbon dioxide;
  d. cooling and then maintaining the erythrocyte concentrate that has been subjected to the gas system at a temperature that is above the freezing point of the erythrocyte concentrate and up to a temperature of about 6° C. for up to 42 days;
  e. agitating said erythrocyte concentrate while in said container i) prior to addition of said gas system to said erythrocyte concentrate, ii) after said addition of said gas system to the erythrocyte concentrate, and combinations thereof; and,
  f. maintaining said erythrocyte concentrate in said container for a period of up to 42 days without considerable degradation of erythrocytes quality and with less than 0.8% hemolysis of said erythrocytes such that said erythrocyte concentrate in said container can be used for said later transfusion.

* * * * *